United States Patent [19]
Gormley et al.

[11] Patent Number: 5,824,686
[45] Date of Patent: *Oct. 20, 1998

[54] METHOD OF TREATING ANDROGENIC ALOPECIA WITH 5-ALPHA REDUCTASE INHIBITORS

[75] Inventors: Glenn J. Gormley; Keith D. Kaufman; Elizabeth Stoner, all of Westfield; Joanne Waldstreicher, Scotch Plains, all of N.J.

[73] Assignee: Merck & Co., Inc., Rahway, N.J.

[*] Notice: The term of this patent shall not extend beyond the expiration date of Pat. Nos. 5,571,817, 5,547,957, and 5,567,708.

[21] Appl. No.: 596,339

[22] PCT Filed: Oct. 11, 1994

[86] PCT No.: PCT/US94/11507

§ 371 Date: Feb. 20, 1996

§ 102(e) Date: Feb. 20, 1996

[87] PCT Pub. No.: WO95/10284

PCT Pub. Date: Apr. 20, 1995

Related U.S. Application Data

[63] Continuation-in-part of Ser. No. 138,520, Oct. 15, 1993, abandoned, and a continuation-in-part of Ser. No. 214,905, Mar. 17, 1994, Pat. No. 5,547,957.

[51] Int. Cl.$^6$ .................................................. A61K 31/44
[52] U.S. Cl. ............................................................ 514/284
[58] Field of Search ............................................. 514/284

[56] References Cited

U.S. PATENT DOCUMENTS

| | | |
|---|---|---|
| 4,377,584 | 3/1983 | Rasmusson et al. . |
| 4,396,615 | 8/1983 | Petrow et al. . |
| 4,684,635 | 8/1987 | Orentreich et al. . |
| 4,760,071 | 7/1988 | Rasmusson et al. . |
| 4,885,289 | 12/1989 | Breuer et al. . |
| 5,053,403 | 10/1991 | Orentreich et al. . |
| 5,175,155 | 12/1992 | Juniewicz et al. . |
| 5,228,431 | 7/1993 | Giaretto . |
| 5,407,944 | 4/1995 | Goldman ................................ 514/310 |
| 5,480,889 | 1/1996 | Goldman ................................ 514/310 |
| 5,547,957 | 8/1996 | Gormley et al. ...................... 514/284 |
| 5,567,708 | 10/1996 | Rasmusson et al. ................... 514/284 |
| 5,571,817 | 11/1996 | Rasmusson et al. ................... 514/284 |

FOREIGN PATENT DOCUMENTS

| | | |
|---|---|---|
| 1302277 | 6/1992 | Canada . |
| 0 004 949 | 10/1979 | European Pat. Off. . |
| 0 155 096 | 9/1985 | European Pat. Off. . |
| 0 285 382 | 10/1988 | European Pat. Off. . |
| WO 92/02225 | 2/1992 | WIPO . |

OTHER PUBLICATIONS

Muller/Kirk Small Animal Dermatology (2nd Ed) (1976) pp. 491–501 ISBN 0–7216–6606X "Alopecias" W.B. Saunders Co. Phila, PA.

Gormley et al., J. Clin. Endo. Metab., vol. 70, pp. 1136–1141 (1990), "Effects of Finasteride (MK–906), a 5alpha–Reductase Inhibitor, on Circulating Androgens in Male Volunteers".

Transcript, WNBC–TV, News 4 NY Live at Five, Nov. 29, 1993.

Diani et al., J. Clin. Endoc. Metab., vol. 74, pp. 345–350 (1992), "Hair Growth Effects of Oral Admin. of Finasteride, a Steroid 5alpha–Reductase Inhibitor . . . ".

Imperato–McGinley et al., J. Clin. Endoc. Metab., vol. 70, pp. 777–782 (1990), "The 5–alpha reductase inhibitor finasteride comparison of male pseudohermaphrodites . . . ".

Bingham et al., J. Endoc., vol. 57, pp. 111–121 (1973), "The metabolism of testosterone by human male scalp skin".

Stoner et al., Prostate, vol. 22, pp. 291–299 (1993), "Finasteride (MK–906) in the treatment of benign prostatic hyperplasia".

Stoner et al., J. Urol., vol. 147, pp. 1298–1302 (1992), "The clinical effects of a 5–alpha–reductase inhibitor, finasteride, on benign prostatic hyperplasia".

Sudduth et al., Pharmacotherapy, vol. 13, pp. 309–325 (Jul.–Aug. 1993), "Finasteride: The first 5–alpha–reductase inhibitor".

Gormley et al., New England J. Med., vol. 327, pp. 1185–1191 (1992), "The effect of finasteride in men with benign prostatic hyperplasia".

Matzkin et al., Clin. Endocrinol., vol. 37, pp. 432–436 (1992), "Prolonged treatment with finasteride (a 5–alpha–reductase inhibitor) dose not affect bone density and metabolism".

McConnell et al., J. Urol., vol. 143, No. 4, Suppl., p. 267A (1990), "The effects of low–dose finsteride (MK–906) on prostatic androgen levels in men with benign prostatic . . . ".

McConnell et al., J. Clin. Endoc. Metab., vol. 74, pp. 505–508 (Mar. 1992), "Finasteride, an inhibitor of 5 alpha–reductase, suppresses prostatic dihydrotestosterone in men . . . ".

Vermeulen et al., Eur. Urol., vol. 20, Supp. 1, pp. 82–86 (1991), "Hormonal effects of 5alpha reductase inhibitor (Finasteride) . . . ".

Vermeulen et al., Prostate, vol. 14, pp. 45–53 (1989), "Hormonal effects of an orally active 4–azasteroid inhibitor of 5–alpha–reductase in humans".

Metacalf et al., Trends Pharmacol. Sci., vol. 10, pp. 491–495 (1989), "Inhibitors of steroid 5–alpha–reductase in benign prostatic hyperplasia, male pattern baldness and acne".

Tempany et al., Prostate, vol. 22, pp. 39–42 (1993), "The influence of finasteride on the volume of the peripheral and periurethral zones of the prostate . . . ".

(List continued on next page.)

Primary Examiner—Shep K. Rose
Attorney, Agent, or Firm—Catherine D. Fitch; Melvin Winokur

[57] ABSTRACT

The instant invention involves a method of treating and/or reversing androgenic alopecia and promoting hair growth, and methods of treating acne vulgaris, seborrhea, and female hirsutism, by administering to a patient in need of such treatment a 5α-reductase 2 inhibitor such as finasteride, in a dosage amount under 5 mgs/day.

5 Claims, No Drawings

OTHER PUBLICATIONS

Diani et al., Chem. Abstracts, vol. 116, Abstract No. 241714e.

Gormley et al., Prob. in Urology, vol. 5, No. 3, pp. 436–440 (1991), "The role of 5alpha–reductase inhibitors in the treatment of benign prostatic hyperplasia".

Rittmaster et al., J. Clin. Endoc. Metab., vol. 65, No. 1, pp. 188–193 (1987), "The effects of N,N–diethyl–4–methyl–3–oxo–4–aza–5alpha–androstane–17beta–carboxamide, a 5alpha–reductase inhibitor and anti-androgen, on the development of baldness . . . ".

Mellin et al., J. Steroid Biochem. Mol. Biol., vol. 44, No. 2, pp. 121–131 (1993), "Azasteroids as inhibitors of testosterone 5alpha–reductase in mammalian skin".

Stoner, J. Steroid Biochem. mol. Biol., vol. 37, No. 3, pp. 375–378 (1990), "The clinical development of a 5alpha–reductase inhibitor, finasteride".

Dallob, J. Clin. Endoc. Metab., vol. 79, No. 3, pp. 703–706 (1994), "The effect of finasteride, a 5alpha–reductase inhibitor, on scalp skin testosterone and dihydrotestosterone concentrations . . . ".

Waldstreicher et al., J. Invest. Derma. 102(4) 1994, p. 615, Item No. 549, "Effects of finasteride on dihydrotestosterone content of scalp skin in men with male pattern baldness".

Shupack et al., Int. J. Dermat. 31(10)1993, pp. 701–706, "Status of medical treatment for androgenetic alopecia".

Kaufman et al., J. Invest. Derma. 102(4) 1994, p. 615, Item No. 550, "Effects of finasteride on dihydrotestosterone content of scalp skin in men with male pattern baldness".

Rhodes et al., J. Clin. Endocrin. & Metab. 79(4), 1994, pp. 991–996, "The effects of finasteride (Proscar) on hair growth, hair cycle stage, and serum testosterone and dihydrotestosterone in adult male and female stumptail macaques (*Macaca arctoides*)".

Steiner, Clin. Pharm. (USA) 12(1) 1993, pp. 15–23, "Finasteride: A 5alpha–reductase inhibitor".

Gormley, Drug Research Reports: The Blue Sheet, vol. 35, No. 20, 1992, pp. 6–7, "Proscar in clincals for chemoprevention following prosatectomy".

Sawaya et al., Dermatol. Clin. (USA) 11(1) 1993, pp. 65–72, "The antiandrogens: when and how they should be used".

METHOD OF TREATING ANDROGENIC ALOPECIA WITH 5-ALPHA REDUCTASE INHIBITORS

This application is the national phase application under 35 U.S.C. § 371 of PCT application Ser. No. PCT/US94/11507, filed Oct. 11, 1994, which is a continuation-in-part of U.S. patent application Ser. No. 08/214,905, filed Mar. 17, 1994 and issued as U.S. Pat. No. 5,547,957 and a continuation in part of Ser. No. 08/138,520, filed Oct. 15, 1993, presently abandoned.

The present invention is concerned with the treatment of androgenic alopecia, including male pattern baldness, with compounds that are 5-alpha reductase isozyme 2 inhibitors.

BACKGROUND OF THE INVENTION

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by an excessive accumulation of testosterone ("T") or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri, et al., *Endocrinol.* 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5α-dihydrotestosterone ("DHT"), formed locally in the target organ by the action of testosterone-5α-reductase. Inhibitors of testosterone-5α-reductase will serve to prevent or lessen symptoms of hyperandrogenic stimulation in these organs. See especially U.S. Pat. No. 4,377,584 assigned to Merck & Co., Inc., issued Mar. 22, 1983. It is now known that a second 5α-reductase isozyme exists, which interacts with skin tissues, especially in scalp tissues. See, e.g., G. Harris, et al., *Proc. Natl. Acad. Sci. USA*, Vol. 89, pp. 10787–10791 (November 1992). The isozyme that principally interacts in skin tissues is conventionally designated as 5α-reductase 1 (or 5α-reductase type 1), while the isozyme that principally interacts within the prostatic tissues is designated as 5α-reductase 2 (or 5α-reductase type 2).

Finasteride (17β-(N-tert-butylcarbamoyl)-4-aza-5α-androst-1-ene-3-one), which is marketed by Merck & Co., Inc. under the tradename PROSCAR®, is an inhibitor of 5α-reductase 2 and is known to be useful for the treatment of hyperandrogenic conditions. See e.g., U.S. Pat. No. 4,760,071. Finasteride is currently marketed in the United States and worldwide for the treatment of benign prostatic hyperplasia. Finasteride's utility in the treatment of androgenic alopecia and prostatic carcinoma is also disclosed in the following documents: EP 0 285,382, published 5 Oct. 1988; EP 0 285 383, published 5 Oct. 1988; Canadian Patent no. 1,302,277; and Canadian Patent no. 1,302,276. The specific dosages exemplified in the above-noted disclosures varied from 5 to 2000 mg per patient per day.

In the treatment of androgenic alopecia, which includes both female and male pattern baldness, and other hyperandrogenic conditions, it would be desirable to administer the lowest dosage possible of a pharmaceutical compound to a patient and still maintain therapeutic efficacy. Applicants have surprisingly and unexpectedly discovered that a low daily dosage of a 5α-reductase 2 inhibitor is particularly useful in the treatment of androgenic alopecia. Furthermore, a low daily dosage of a 5α-reductase 2 inhibitor may also be particularly useful in the treatment of the hyperandrogenic conditions of acne vulgaris, seborrhea, female hirsutism, and polycystic ovary syndrome.

DETAILED DESCRIPTION OF THE INVENTION

The instant invention involves a method of treating and/or reversing androgenic alopecia and promoting hair growth, and methods of treating acne vulgaris, seborrhea, and female hirsutism, which comprises administering to a patient in need of such treatment a 5α-reductase 2 inhibitor in a dosage amount under 5 mgs/day. In one embodiment of this invention, the 5α-reductase 2 inhibitor is administered in a dosage amount of from 0.01 to 3.0 mgs/day. In one class of this embodiment, the 5α-reductase 2 inhibitor is administered in a dosage amount of from 0.05 to 1.0 mg/day, and in a sub-class of this embodiment, the 5α-reductase 2 inhibitor is administered in dosage amounts of about 0.05 to 0.2 mg/day. Illustrating this subclass are dosage amounts of about 0.05, 0.1, 0.15 and 0.2 mg/day. Exemplifying the sub-class are dosages of 0.05 and 0.2 mg/day. Compounds which are inhibitors of 5α-reductase 2 can be determined by employing the assay described below in Example 3.

In a second embodiment of this invention, the method of treating androgenic alopecia comprises administration of 5α-reductase 2 inhibitor compounds which have the structural Formula I

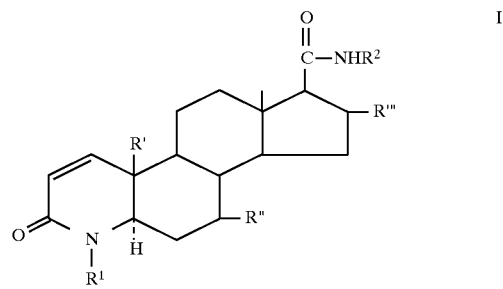

or a pharmaceutically acceptable salt thereof wherein:

$R^1$ is hydrogen, methyl or ethyl;

$R^2$ is a hydrocarbon radical selected from straight and branched chain alkyl of from 1–12 carbons or monocyclic aryl optionally containing 1 or more lower alkyl substituent of from 1–2 carbon atoms and/or 1 or more halogen (Cl, F or Br) substituents;

R' is hydrogen or methyl;

R" is hydrogen or β-methyl; and

R'" is hydrogen, α-methyl or β-methyl.

In one class of this second embodiment, the 5α-reductase 2 inhibitor compounds have the structural Formula II

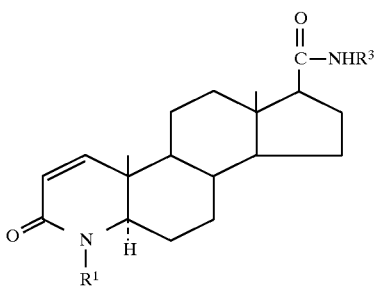

or a pharmaceutically acceptable salt thereof wherein $R^1$ is hydrogen, or methyl; and $R^3$ is branched chain alkyl of from 4–8 carbons.

Representative compounds that may be employed in the present invention include the following:

17β-(N-tert-butylcarbamoyl)-4-aza-5-α-androst-1-en-3-one,

17β-(N-isobutylcarbamoyl)-4-aza-5-α-androst-1-en-3-one,

17β-(N-tert-octylcarbamoyl)-4-aza-5α-androst-1-en-3-one,

17β-(N-octylcarbamoyl)-4-aza-5α-androst-1-en-3-one,

17β-(N-1,1-diethylbutylcarbamoyl)-4-aza-5-α-androst-1-en-3-one,

17β-(N-neopentylcarbamoyl)-4-aza-5α-androst-1-en-3-one,

17β-(N-tert-arnylcarbamoyl-4-aza-5α-androst-1-en-3-one, and

17β-(N-tert-hexylcarbamoyl)-4-aza-5α-androst-1-en-3-one; and the corresponding compounds wherein the 4-nitrogen is substituted in each of the above named compounds by a methyl or an ethyl radical.

Also included as representative compounds are any of the above indicated compounds having the N-branched chain alkyl substituent replaced by a methyl, ethyl, propyl, i-propyl, butyl, phenyl; 2, 3 or 4 tolyl, xylyl, 2-bromo or 2-chlorophenyl, 2-6-dichloro, or a 2,6-dibromophenyl substituent.

The compounds of Formula I and II described above can be synthesized according to procedures well known in the art, and which are described, for example, in U.S. Pat. No. 4,760,071, EP 0 285,382 and EP 0 285 383. The compound finasteride is currently available as a prescription pharmaceutical from Merck & Co. Inc. The synthesis of finasteride is described in U.S. Pat. No. 4,760,071. A further synthesis of finasteride is described in *Synthetic Communications*, 30 (17), p. 2683–2690 (1990).

The present invention has the objective of providing methods of treating the hyperandrogenic conditions of androgenic alopecia, including male pattern baldness and female pattern baldness, acne vulgaris, seborrhea, female hirsutism, and polycystic ovary syndrome by systemic, oral, parenteral or topical administration of a 5α-reductase 2 inhibitor in a dosage amount under 5 mg/day, and particularly, from about 0.01 mg/day to 3.0 mg/day, and more particularly 0.05 to 1 mg/day. The invention is further illustrated by dosages of about 0.05 to 0.2 mg/day and specifically dosages of about 0.05, 0.1, 0.15 and 0.2 mg/day. Exemplifying the invention are dosages of 0.05 and 0.2 mg/day. The term "treating androgenic alopecia" is intended to include the arresting and/or reversing of androgenic alopecia, and the promotion of hair growth. Also, a 5α-reductase 2 inhibitor, e.g., finasteride, at a dosage under 5 mgs/day can be used in combination with a potassium channel opener, such as minoxidil or a pharmaceutically acceptable salt thereof, for the treatment of androgenic alopecia, including male pattern baldness. The 5α-reductase 2 inhibitor and the potassium channel opener may both be applied topically, or each agent can be given via different administration routes; for example, the 5α-reductase 2 inhibitor may be administered orally while the potassium channel opener may be administered topically.

The present invention also has the objective of providing suitable systemic, oral, parenteral and topical pharmaceutical formulations for use in the novel methods of treatment of the present invention. The compositions containing 5α-reductase 2 inhibitor compounds as the active ingredient for use in the treatment of the above-noted hyperandrogenic conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions. Likewise, they may also be administered in intravenous (both bolus and infusion), intraperitoneal, subcutaneous, topical with or without occlusion, or intramuscular form, all using forms well known to those of ordinary skill in the pharmaceutical arts. For oral administration, for example, the compositions can be provided in the form of scored or unscored tablets containing 0.01, 0.05, 0.1, 0.2, 1.0, 2.0 and 3.0 milligrams of the active ingredient for the symptomatic adjustment of the dosage to the patient to be treated.

For the treatment of androgenic alopecia including male pattern baldness, acne vulgaris, seborrhea, and female hirsutism, the 5α-reductase 2 inhibitor compounds may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 0.1% of the active compound in admixture with a pharmaceutically acceptable carrier.

Advantageously, compounds of the present invention may be administered in a single daily dose, or the total daily dosage may be administered in divided doses of two, three or four times daily. The compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the 5α-reductase 2 inhibitor compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, propylene glycol, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The following example illustrates the present invention and as such are not to be considered as limiting the invention set forth in the claims appended hereto.

EXAMPLE 1

Finasteride is known to occur in two distinct polymorphic crystal forms, termed "Form I" and "Form II". Form I is the marketed form of finasteride as a 5 mg tablet (PROSCAR®).

Finasteride Form I can be prepared by dissolving finasteride in glacial acetic acid (ca. 100 mg/ml) and adding water with stirring until the weight % of water equals or exceeds 84%. The resulting solid phase is collected by filtration and dried under vacuum and at about 50° C. The resulting Form I is characterized by a differential scanning calorimetry (DSC) curve, at heating rate of 20° C./min and in a closed cup, exhibiting a minor endotherm with a peak temperature of about 232° C., an extrapolated onset temperature of about 223° C. with an associated heat of about 11 joules/gm and by a major melting endotherm with a peak temperature of about of 261° C., an extrapolated onset temperature of about 258° C. with an associated heat of about 89 J/gm. The x-ray powder diffraction pattern is characterized by d-spacings of 6.44, 5.69, 5.36, 4.89, 4.55, 4.31, 3.85, 3.59 and 3.14. The FT-IR spectrum shows bands at 3431, 3237, 1692, 1666, 1602 and 688 cm-1. The solubilities in water and cyclohexane at 25° C. are 0.05+0.02 and 0.27+0.05 mg/gm respectively. In addition, Form I of finasteride can be prepared by recrystallization from dry ($H_2O$<1 mg/ml) ethyl acetate and isopropyl acetate. The isolated solids are dried under vacuum at about 50° C. and have the same physical characterization data as given above.

EXAMPLE 2

Form II of finasteride can be prepared by dissolving finasteride in glacial acetic acid (ca. 100 mg/ml) and adding water with stirring until the weight % of water equals about 75% but not in excess of 80%. The resulting solid phase is collected by filtration and dried under vacuum and at about 100° C. The resulting Form II is characterized by a DSC curve, at heating rate of 20° C./min and in a closed cup, exhibiting a single melting endotherm with a peak temperature of about of 261° C., an extrapolated onset temperature of about 258° C. with an associated heat of about 89 J/gm. The x-ray powder diffraction pattern is characterized by d-spacings of 14.09, 10.36, 7.92, 7.18, 6.40, 5.93, 5.66, 5.31, 4.68, 3.90, 3.60 and 3.25. The FT-IR spectrum shows bands at 3441, 3215, 1678, 1654, 1597, 1476 and 752 cm-1. The solubilities in water and cyclohexane at 25° C. are 0.16+0.02 and 0.42+0.05 mg/gm respectively. In addition, Form II of finasteride can be prepared by recrystallization from ethyl acetate containing between 2 to 30 mg/ml of water and isopropyl acetate containing between 2 to 15 mg/ml of water. The isolated solids are dried under vacuum at about 80° C. and have the same physical characterization data as given above. Form II can also be prepared by heating Form I up to about 150° C., holding for about one hour and cooling back to room temperature. The Form II prepared in this manner has the same physical characterization data as given above.

EXAMPLE 3
Preparation of Human prostatic 5α-reductase.

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic reductases were stable for at least 4 months when stored under these conditions.

5α-reductase assay

The reaction mixture for the type 2 5α-reductase contained 40 mM sodium citrate, pH 5.5, 0.3 μM [7-$^3$H]-testosterone, 1 mM dithiothreitol and 500 μM NADPH in a final volume of 100 μl. Typically, the assay was initiated by the addition of 50–100 μg prostatic homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate preparation were T, DHT and androstanediol.

Inhibition studies

Compounds were dissolved in 100% ethanol. IC$_{50}$ values represent the concentration of inhibitor required to decrease enzyme activity to 50% of the control. IC$_{50}$ values were determined using a 6 point titration where the concentration of the inhibitor was varied from 0.1 to 1000 nM.

EXAMPLE 4

Macrophotography And Global Photography Procedure For Detection Of Hair Growth

A. Macrophotographic Procedure
Location: ID card
  Haircount target area
Equipment: Film: Kodak-T-max 24 exposure each of same emulsion lot number
Camera: Nikon N-6000
Lens: Nikkor 60 mm f2.8
Flashes: Nikon SB-21B Macroflash
Device: registration device
Photographic Procedure:
  In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly anterior to the center of the vertex bald spot, using a commercial tattooing machine or manually (needle and ink). An area approximately one square inch in size, centered at the tattoo at the leading edge of the balding area, is clipped short (~2 mm). Cut hairs are removed from the area to be photographed, using tape. Compressed air and/or ethanol wipes may also be used to facilitate removal of cut hairs.
2. Magnification: Each lens supplied has a fixed reproduction ratio of 1:1.2.
   Aperture: Every photograph is taken at f/22.
   Film: T-Max 100 (24 exposure) is used.
3. Patient's haircount target area. Three exposures (−2/3, 0, and +2/3 f-stop).

A trained technician places a transparency over the photographic print and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and DeLong, E., *J. American Academy of Dermatology*, Vol. 23, p. 470 (1990).

B. Global Photographic Procedure
Locations: Color card/patient Id
  Global photograph
Equipment: Film: Kodachrome KR-64 24 exposure each of same emulsion lot number
Camera: Nikon N-6000
Lens: Nikkor 60 mm f2.8
Flashes: Nikon SB-23
Photographic Procedure
  In these clinical photographs, the only variable allowed is the global area's appearance. Anything extraneous to the area (clothing, furniture, walls, etc.) is eliminated from the fields to be photographed.

1. Patients will have global photographs taken prior to hair clipping with the head in a fixed position (determined by the supplied stereotactic device). Hair on the patient's head is positioned consistently so as to not obscure the bald area.
2. Magnification: Each lens supplied has a fixed reproduction ratio of 1:6.
   Aperture: Every photograph will be taken at f/11.
   Film: Kodachrome (24 exposure) is used.
3. Patient's global photographs. Three exposures at zero compensation.

Using the above-described methodology, it can be shown that administration of 5α-reductase 2 inhibitors, including finasteride, in dosages below 5 mg/day per patient, for example, 1 mg/day or 0.2 mg/day, are useful in the treatment of androgenic alopecia, and promote hair growth in patients with this condition.

EXAMPLE 5

In another test, finasteride was orally administered for 6 weeks to men with male pattern baldness at doses of 0.2 mg/day, 1.0 mg/day and 5.0 mgs/day. The results of this test showed a significant reduction in DHT content in scalp tissue of the test participants.

What is claimed is:

1. A tablet useful for the treatment of androgenic alopecia, consisting essentially of 17β-(N-tert-butylcarbamoyl)-4-aza-5alpha-androst-1-ene-3-one as the active ingredient wherein the dosage is about 0.05 to 3.0 mg.

2. The tablet of claim 1 wherein the dosage is about 1.0 mg.

3. A pharmaceutical composition adapted for oral administration for the treatment of male pattern baldness consisting essentially of a unit dosage amount of 0.05 to 1.0 mg 17β-(N-tert-butylcarbamoyl)-4-aza-5alpha-androst-1-ene-3-one as the active ingredient and a pharmaceutically acceptable carrier.

4. The pharmaceutical composition of claim 3 consisting essentially of a unit dosage amount of about 1 mg 17β-(N-tert-butylcarbamoyl)-4-aza-5alpha-androst-1-ene-3-one as the active ingredient and a pharmaceutically acceptable carrier.

5. A tablet useful for the treatment of male pattern baldness consisting essentially of 17β-(N-tert-butylcarbamoyl)-4-aza-5alpha-androst-1-ene-3-one as the active ingredient wherein the dosage is about 1.0 mg.

* * * * *